(12) United States Patent
Malhotra et al.

(10) Patent No.: US 10,307,432 B2
(45) Date of Patent: *Jun. 4, 2019

(54) STABILIZED LIQUID FOSAPREPITANT FORMULATIONS

(71) Applicant: Cipla Limited, Mumbai (IN)

(72) Inventors: Geena Malhotra, Mumbai (IN); Sarabjit Singh, Maharashtra (IN); Abhijit Jadhav, Maharashtra (IN)

(73) Assignee: Cipla Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/886,247

(22) Filed: Feb. 1, 2018

(65) Prior Publication Data

US 2018/0153913 A1 Jun. 7, 2018

Related U.S. Application Data

(63) Continuation of application No. 15/342,445, filed on Nov. 3, 2016, now Pat. No. 9,913,853.

(30) Foreign Application Priority Data

Nov. 3, 2015 (IN) .......................... 4180/MUM/2015

(51) Int. Cl.
| | |
|---|---|
| *A61K 31/675* | (2006.01) |
| *A61K 47/18* | (2017.01) |
| *A61K 9/00* | (2006.01) |
| *A61K 45/06* | (2006.01) |
| *A61K 9/08* | (2006.01) |

(52) U.S. Cl.
CPC .......... *A61K 31/675* (2013.01); *A61K 9/0019* (2013.01); *A61K 45/06* (2013.01); *A61K 47/183* (2013.01); *A61K 9/08* (2013.01)

(58) Field of Classification Search
CPC ........................... C07F 9/65181; A61K 9/675
USPC ............................................ 514/93
See application file for complete search history.

(56) References Cited

U.S. PATENT DOCUMENTS

| | | | |
|---|---|---|---|
| 5,538,982 A | 7/1996 | Hagan et al. | |
| 9,913,853 B2 * | 3/2018 | Malhotra | ............. A61K 31/675 |
| 2007/0265329 A1 | 11/2007 | Devang et al. | |
| 2013/0317016 A1 | 11/2013 | Hingorani et al. | |
| 2014/0107337 A1 | 4/2014 | Reddy et al. | |
| 2015/0165045 A1 | 6/2015 | Diakidou et al. | |
| 2017/0239335 A1 | 8/2017 | Sonavaria | |

FOREIGN PATENT DOCUMENTS

| | | |
|---|---|---|
| CN | 102379845 | 3/2012 |
| EP | 0748320 | 12/1996 |
| WO | 2014093907 | 6/2014 |
| WO | 2016059590 | 4/2016 |

\* cited by examiner

*Primary Examiner* — Raymond J Henley, III

(74) *Attorney, Agent, or Firm* — Meunier Carlin & Curfman LLC

(57) ABSTRACT

The present invention relates to stable pharmaceutical compositions of fosaprepitant or a salt thereof in the form of ready-to-use or ready-to-dilute compositions suitable for parenteral administration.

21 Claims, 2 Drawing Sheets

STABILIZED LIQUID FOSAPREPITANT FORMULATIONS

CROSS REFERENCE TO RELATED APPLICATION

This application is a continuation of U.S. application Ser. No. 15/342,445, filed Nov. 3, 2016, now U.S. Pat. No. 9,913,853, which claims the benefit of Indian Application 4180/MUM/2015, filed on Nov. 3, 2015.

FIELD OF THE INVENTION

The present invention relates to pharmaceutical liquid compositions of the neurokinin 1 (NK1) receptor antagonist fosaprepitant and related compounds with enhanced stability against degradation.

BACKGROUND

Nausea and vomiting are common and feared symptoms among cancer patients; up to 80% of patients experience chemotherapy-induced nausea and vomiting (CINV) without prophylactic therapy. The syndrome may have a significant impact on the treatment and quality of life as patients may delay or even cancel scheduled chemotherapies. Generally, CINV syndrome can be categorized as acute, delayed or anticipatory. In acute CINV, nausea and vomiting appear within the first 24 hours after chemotherapy, while in the case of delayed CINV, symptoms can last for several days. Anticipatory CINV is a conditional response that occurs in patients who had poorly controlled CINV symptoms during a previous course of chemotherapy.

Until recently the prevention and treatment of CINV symptoms involved the use of corticosteroids, dopamine D2 antagonists and serotonin 5-HT3 receptor antagonists. Therapies consisting of serotonin 5-HT3 receptors (such as Kytril® (granisetron), Zofran® (ondansetron), Anzemet® (dolesetron), Aloxi® (palonosetron) and Navoban® (Tropisetron)). Aloxi® (palonosetron), due to its longer half-life, is the only serotonin 5-HT3 receptor antagonist currently approved for the prevention of both acute and delayed CINV. Usually, a combination of Aloxi® and a corticosteroid, administrated prior to chemotherapy, followed by administration of one or both agents for several days is used for the prevention of delayed CINV. However, unpleasant adverse-effects due to the multiple dosing of 5-HT3 receptor antagonist during the treatment of delayed CINV symptoms, such as headache and constipation, led to the addition of neurokinin 1 (NK1) receptor antagonists, such as Aprepitant or Fosaprepitant, in the treatment regimen.

Aprepitant is a highly-selective antagonist of NK1 receptors with little or no affinity for serotonin, dopamine or corticosteroid receptors. It is available in the form of capsules for oral administration (Emend®) containing either 40 mg, 80 mg, or 125 mg of aprepitant. Unfortunately, oral capsule formulations are easy to swallow for patients undergoing chemotherapy or postoperative condition since such capsules themselves often induce nausea and vomiting.

Fosaprepitant is a water-soluble phosphorylated prodrug of aprepitant, which may be administered intravenously. Fosaprepitant has been reported to undergo rapid conversion to aprepitant in less than 30 minutes after an IV infusion.

Fosaprepitant Dimeglumine for Injection (Emend® for Injection) is sold as a lyophilized prodrug of aprepitant. To administer, a small about of saline is combined with the lyophilized powder, and then transferred to an infusion bag to yield a final concentration of 1 mg/ml. Care must be taken during the initial dilution to prevent foaming. The reconstituted final drug solution is reported to be stable only for 24 hours at ambient room temperature (at or below 25° C.) after reconstitution. One of the primary degradation products is aprepitant. As aprepitant is generated, it will precipitate from an aqueous solution. This poses a challenge in preparing ready-to-use or ready-to-dilute compositions of Fosaprepitant dimeglumine.

It is an object of the invention to provide a stable ready-to-use liquid compositions of fosaprepitant suitable for parenteral administration. It is an object of the invention to provide a stable ready-to-dilute liquid compositions of fosaprepitant for parenteral administration. It is an object of the invention to provide liquid compositions of fosaprepitant which do not degrade to aprepitant. It is an object of the invention to provide a stable composition of fosaprepitant containing less than 10% w/v of aprepitant, even when stored over prolonged periods of time.

The details of one or more embodiments are set forth in the descriptions below. Other features, objects, and advantages will be apparent from the description and from the claims.

DETAILED DESCRIPTION

Figure 1:
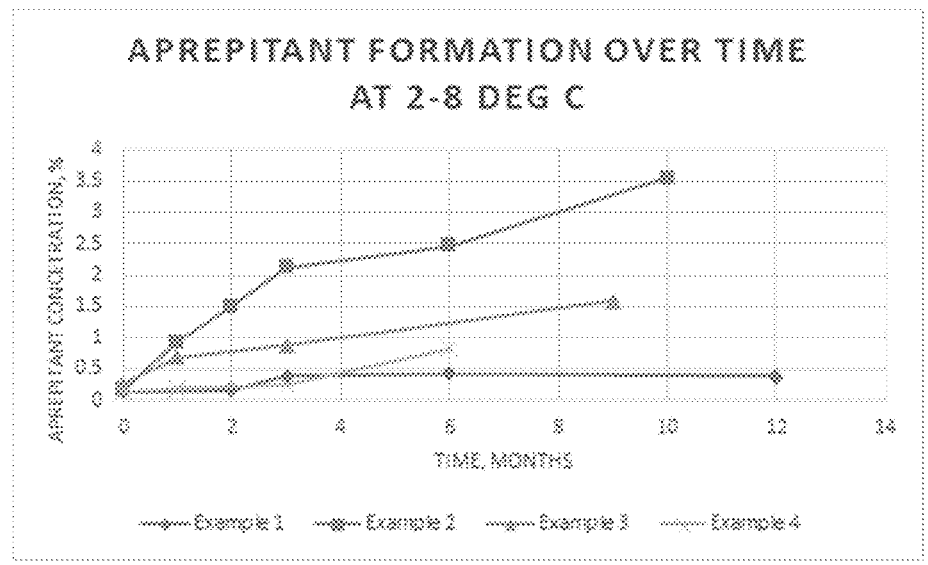
FIG. 1: Aprepitant Formation over time at 2-8° C. in fosaprepitant compositions.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The term "aprepitant" or "fosaprepitant" includes not only "aprepitant" or "fosaprepitant" per se but also its pharmaceutically acceptable derivatives such as pharmaceutically acceptable salts, pharmaceutically acceptable solvates, pharmaceutically acceptable hydrates, pharmaceutically acceptable anhydrates, pharmaceutically acceptable esters, pharmaceutically acceptable polymorphs, pharmaceutically acceptable tautomers, pharmaceutically acceptable complexes etc. Preferably, fosaprepitant is present in the form of dimeglumine salt.

The term "ready-to-use" refers to any liquid composition of Fosaprepitant, optionally comprising other pharmaceutically acceptable excipients, in the form of a solution, suspension or emulsion wherein the composition does not require any reconstitution or dilution with parenterally acceptable diluent and can be directly administered to the patient.

The term "ready-to-dilute" or "concentrate ready for dilution" refers to any liquid composition of fosaprepitant, optionally comprising other pharmaceutically acceptable excipients, in the form of a solution, suspension or emulsion in which the composition can be wherein further diluted with a suitable solvent for parenteral administration before administering to the patient.

The term "stable" refers to any composition of Fosaprepitant wherein no precipitation of aprepitant is observed such that the composition remains clear and has sufficient stability to allow storage at a convenient temperature and relative humidity (RH), such as between about 0° C. and about 60° C. and about 20% to 75% RH, for a reasonable period of time, such as at least about one week, at least about one month, at least about three months, at least about six months, at least about one year, or at least about 2 years. In contrast, commercially available Emend® for Injection substantially degrades after dilution in this time period. In certain embodiments, stabilized fosaprepitant formulations will develop less than 10% w/v of aprepitant of the total composition over a period of time. For instance, after a stabilized liquid formulation is stored at 2-8° C. for a period of at least 1 month, no more than 10%, 5% or 2.5% aprepitant will be generated. In some embodiments, after a stabilized liquid formulation is stored at 2-8° C. for a period of at least six months, no more than 10%, 5% or 2.5% aprepitant will be generated. The said stable compositions of Fosaprepitant comprise not more than 10% w/v of aprepitant over the storage period, either in free form or in the form bound to albumin. In a preferred embodiment, the said stable compositions of Fosaprepitant comprise not more than 5% w/v of aprepitant over the storage period, either in free form or in the form bound to albumin. In a more preferred embodiment, the said stable compositions of Fosaprepitant comprise not more than 3% w/v of aprepitant over the storage period, either in free form or in the form bound to albumin.

The ready-to-use compositions of fosaprepitant are stable in aqueous medium/vehicle for at least 30 days with no aprepitant precipitation, for instance, as measured by visual inspection.

The term "parenteral" or "injectable" refers to routes selected from subcutaneous (SC), intravenous (IV), intramuscular (IM), intradermal (ID), intraperitoneal (IP) and the like.

In an embodiment of the invention, the ready-to-use or ready-to-dilute compositions may be formulated as aqueous or non-aqueous solutions, suspensions or emulsions.

The pharmaceutical compositions of the present invention comprise one or more pharmaceutically acceptable liquid excipient(s) selected from, but are not limited to, solvents/co-solvents, surfactants, solubilizers, wetting agents, water immiscible solvents, water, water miscible solvents, oily components, hydrophilic solvents, hydrophobic solvents, emulsifiers, preservatives, chelating agents, antioxidants, anti-foaming agents, buffering agents, pH adjusting agents, osmotic agents, channel forming agents, osmotic adjustment agents, and the like or mixtures thereof.

The pharmaceutical compositions of the present invention may further comprise one or more stabilizers.

The ready-to-use or ready-to-dilute compositions may be sterile injectable solutions, suspensions or emulsions in a nontoxic, parenterally acceptable vehicle. Exemplary vehicles include, but are not limited to, water for injection, isotonic dextrose solution, albumin solution (5%, 10%, or 25%), Ringer's solution, and isotonic sodium chloride solution.

Preferably, the vehicle comprises albumin solution (5%, 10%, or 25%). Suitable albumin solution that may be employed include, but are not limited to, commercially available albumin preparations, such as Albuminar® (Centeon/Aventis Behring), Buminate® (Baxter Laboratories), Plasbumin® (Bayer Biological), AlbuRx® (CSL Behring), Albutein® (Alpha Therapeutic), Albumin (Human) (Immuno-U.S.), Albumarc® (American Red Cross), Human Serum Albumin (Swiss Red Cross) and the like. The commercially available albumin preparations comprise pharmaceutically acceptable excipient(s) such as sodium N-acetyl-tryptophanate, sodium caprylate, sodium chloride, sodium bicarbonate, sodium hydroxide, or acetic acid, and the like or mixtures thereof.

Alternatively, albumin solution can be prepared by mixing albumin powder in water along with other pharmaceutically acceptable excipient(s) as available in the commercially available albumin products. Albumin may be natural in origin or synthetically prepared.

Preferably, the ready-to-use or ready-to-dilute compositions will include a vehicle in an amount from about 0 ml to greater than or equal to 200 ml. Ready-to-dilute formulations typically have lower amounts of vehicle, e.g., no more than 5 ml, no more than 10 ml or no more than 15 ml. In some embodiments, the ready-to-dilute compositions does not comprise any vehicle. Ready-to-use formulations, on the other hand, will typically have higher amounts for vehicle. For instance, a ready-to-use formulation can include vehicle in an amount from 75-200 ml, 100-200 ml, 100-150 ml Suitable solubilizers that may be employed include, but are not limited to, various solvents such alcohols (ethanol, octanol, glycofurol), various glycols (propylene glycol, polyethylene glycol, glycerol etc.), and aprotic solvents such as dimethylacetamide, Isopropyl myristate, dimethyl sulphoxide (DMSO), dimethyl isosorbide, methylene chloride, triacetin, diacetin, tributyrin, triethyl citrate, acetyl triethyl citrate, acetyl tributyl citrate, triethylglycerides, triethyl phosphate, diethyl phthalate, diethyl tartrate, mineral oil, polybutene, silicone fluid, ethyl lactate, N-methyl-2-pyrrolidone, 2-pyrrolidone, methyl acetate, ethyl acetate, methyl ethyl ketone, dimethyl formamide, tetrahydrofuran, caprolactam, and 1-dodecylazacyclo-heptan-2-one, and the like or mixtures thereof.

Preferably, the ready-to-use or ready-to-dilute compositions comprise solubilizers in an amount from about 0 to about 5 ml of the total composition.

Suitable wetting agents or surfactants include, but are not limited to, amphoteric, non-ionic, cationic or anionic molecules. Suitable surfactants include, but are not limited to, polysorbates, sodium dodecyl sulfate (sodium lauryl sulfate), lauryl dimethyl amine oxide, docusate sodium, cetyl trimethyl ammonium bromide (CTAB), polyethoxylated alcohols, polyoxyethylene sorbitan, octoxynol, N,N-dimethyldodecylamine-N-oxide, hexadecyltrimethylammonium bromide, polyoxyl 10 lauryl ether, Brij® surfactants (polyoxyethylene vegetable-based fatty ethers derived from lauryl, cetyl, stearyl and oleyl alcohols), bile salts (such as sodium deoxycholate and sodium cholate), polyoxyl castor oil, nonylphenol ethoxylate, cyclodextrins, lecithin, phospholipids (such as phosphatidylcholine, phosphatidylethanolamine, phosphatidylserine, phosphatidylinositol, etc.), methylbenzethonium chloride, carboxylates, sulphonates, petroleum sulphonates, alkylbenzenesulphonates, naphthalenesulphonates, olefin sulphonates, alkyl sulphates, sulphates, sulphated natural oils and fats, sulphated esters, sulphated alkanolamides, alkylphenols (ethoxylated and sulphated), ethoxylated aliphatic alcohol, polyoxyethylene surfactants, carboxylic esters, polyethylene glycol esters, anhydrosorbitol ester and ethoxylated derivatives thereof, glycol esters of fatty acids, carboxylic amides, monoalkanolamine condensates, polyoxyethylene fatty acid amides, quaternary ammonium salts, amines with amide linkages, polyoxyethylene alkyl and alicyclic amines, N,N,N,N tetrakis substituted ethylenediamines, 2-alkyl 1-hydroxyethyl 2-imidazolines, N-coco 3-aminopropionic acid/sodium salt N-tallow-3-iminodipropionate disodium salt, N-carboxymethyl-N-dimethyl N-9 octadecenyl ammonium hydroxide, N-cocoamidethyl n-hydroxyethylglycine sodium salt and the like, polyoxyethylene, sorbitan monolaurate and stearate, cremophor® (polyethoxylated castor oil), Solutol® (ethylene oxide/12-hydroxy stearic acid), Kolliphor HS-15® (Macrogol-15-hydroxystearate), polysorbates, tyloxapol and the like or mixtures thereof.

Preferably, the ready-to-use or ready-to-dilute compositions comprise surfactants in an amount from about 0 to about 5 ml of the total composition.

Suitable polymers include, but are not limited to, cellulose derivatives (such as hydroxypropylcellulose, hydroxymethylcellulose, hydroxypropylmethylcellulose, methylcellulose polymers, hydroxyethylcellulose, sodium carboxymethylcellulose, carboxymethylene and carboxymethyl hydroxyethylcellulose or any combination thereof); and acrylics (such as acrylic acid, acrylamide, and maleic anhydride polymers, copolymers or their mixtures thereof) and the like or mixtures thereof.

Suitable oils include, but are not limited to, castor oil, medium chain triglycerides (MCTs), mineral oils, vegetable oils, oily fatty acids, oily fatty alcohols, esters of sorbitol, fatty acids, oily sucrose esters, and the like any mixtures thereof. Examples of suitable vegetable oils include cotton seed oil, ground nut oil, corn oil, germ oil, olive oil, palm oil, soybean oil, sweet almond oil, sesame oil, and the like any mixtures thereof. Examples suitable of mineral oils include silicone oil, petrolatum oil, liquid paraffin and the like or any mixtures thereof. Examples of suitable medium chain triglycerides include coconut oil; hydrogenated oils comprising hydrogenated cottonseed oil, hydrogenated palm oil, hydrogenated castor oil, hydrogenated soybean oil and the like or any mixtures thereof.

Suitable anti-foaming agents include, but are not limited to, silicon emulsions or sorbitan sesquioleate and the like or mixtures thereof.

Suitable stabilizers to prevent or reduce the deterioration of the components in the compositions of the present invention include, but are not limited to; metal salts of fatty acids, e.g., $MO_2C-R$, wherein M is metal such as lithium, sodium, potassium, magnesium, or calcium, and R is an alkyl group having from 4-20 carbons, e.g., 4-18 carbons, 4-16 carbons, 6-16 carbons or 6-14 carbons. R may include one or more elements of unsaturation such as an olefinic bond. Exemplary fatty acid salts include sodium caprylate; sodium N-acetyltryptophanate; antioxidants such as, but are not limited to, glycine, α-tocopherol, a-tocopherol polyethylene glycol succinate (Vitamin E TPGS), ascorbic acid, propyl gallate, butylated hydroxy anisole (BHA), butylated hydroxy toluene (BHT), and the like or mixtures thereof; chelating agents such as, but are not limited to, salts of ethylenediaminetetraacetic acid (EDTA) such as disodium ethylenediaminetetraacetate (edetate disodium), tetrasodium and trisodium ethylenediaminetetraacetate ($Na_4$EDTA and $Na_3$EDTA), hydroxyethylethylenediaminetriacetate (HEDTA), diethylenetriaminepentaacetate (DTPA), nitrilotriacetate (NTA), ethanoldiglycine disodium salt (EDG), diethanolglycine sodium-salt (DEG), and 1,3-propylenediaminetetraacetic acid (PDTA).

Preferably, the ready-to-use or ready-to-dilute compositions will include one or more stabilizers in an amount from about 0 to about 500 mg.

The ready-to-use and ready-to-dilute compositions can include one or more tonicity modifies, buffering agents, preservatives and the like. Suitable tonicity modifiers include, but are not limited to, mannitol, sodium chloride, glucose and the like or mixtures thereof. Suitable buffering agents include, but are not limited to, acetates, phosphates, citrates with suitable cations and the like or mixtures thereof. Suitable preservatives include, but are not limited to, benzalkonium chloride, benzethonium chloride and cetyl pyridinium chloride, benzyl bromide, benzyl alcohol, phenyl mercury nitrate, phenyl mercury acetate, thimerosal, merthiolate, acetate and phenyl mercury borate, polymyxin B sulphate, chlorhexidine, methyl and propyl parabens, phenylethyl alcohol, quaternary ammonium chloride, sodium benzoate, sodium propionate, stabilized oxychloro complex, sorbic acid and the like or their mixtures thereof.

In a preferred embodiment of the invention, the composition is formulated to have a pH range of 4.5 to 10.0, and more preferably a pH of 7.0 to 9.0. Suitable pH adjusting agents include, but are not limited to, diethanolamine, triethanolamine, sodium hydroxide, hydrochloric acid, citric acid and monobasic sodium phosphate and the like or their mixtures thereof.

According to present invention, the ready-to-use or ready-to-dilute compositions will contain fosaprepitant dimeglumine at concentrations from about 0.5 mg/mL to about 200 mg/mL, preferably from about 1 mg/mL to about 10 mg/mL, more preferably about 1 mg/mL. Alternatively, the ready-to-use or ready-to-dilute compositions include from about 50-250 mg fosaprepitant dimeglumine. Preferably, the ready-to-use or ready-to-dilute compositions comprise 245.3 mg of fosaprepitant dimeglumine of the total composition.

In some embodiments, the compositions can contain from about 50-250 mg fosaprepitant meglumine, from 10-100 mg of at least one salt of ethylenediaminetetraacetic acid, for instance, the disodium salt, from 200 mg to 100 g of albumin, and from 3-300 ml of water. The compositions can also contain additional antioxidants, stabilizers, pH adjusters, tonicity modifiers, buffers and the like. In certain embodiments, the ratio of albumin to water can be from 1:100 1:2, from 1:50 to 1:2, from 1:25 to 1:2 w/w, from 1:10 to 1:2, from 1:8 to 1:2, from 1:6 to 1:2, or from 1:5 to 1:3. In some instance, the ratio of albumin to water is about 1:4 (w/w). In ready-to-dilute embodiments, the formulations can be diluted with aqueous albumin to give ready-to-use compositions with similar ratios of albumin to water. In instances where the ready-to-dilute formulation is diluted with vehicles not containing albumin (e.g., saline, Ringer's solution, and the like), the final ratio of albumin to water (w/w) can be from 1:250 to 1:25, from 1:250 to 1:50, from 1:200 to 1:50, from 1:200 to 1:100, or from 1:175 to 1:125.

The pharmaceutical compositions may be sterilized by methods known in the art. The compositions may undergo aseptic filtration (e.g., using a 0.2 µm disposable pre-sterilized membrane filter). Additionally, the composition may be placed into a container (e.g., an intravenous solution bag, bottle, vial, ampoule, or pre-filled sterile syringe). The container may have a sterile access port for piercing by a hypodermic injection needle. In some embodiments, the composition may be filled in one or more pre-sterilized depyrogeneated vials and stoppered aseptically with a pre-sterilized butyl stopper.

According to the present invention, the ready-to-dilute compositions may be provided in a kit form along with parenterally acceptable diluent. Parenterally acceptable diluents include water for injection, 0.9% saline (normal saline), 0.45% saline (half normal saline), 2.5% dextrose/0.45% saline and albumin solution (5%, 10%, or 25%).

In an embodiment of the invention, there is provided a method for treating CINV by administering the stable ready-to-use or ready-to-dilute pharmaceutical composition of Fosaprepitant dimeglumine using a suitable dosage level from about 0.001 to 10 mg/kg per day, preferably about 0.005 to 5 mg/kg per day, and especially about 0.05 to 5 mg/kg per day. The compositions may be administered on a regimen of 1 to 4 times per day, preferably once per day.

For the treatment of certain conditions it may be desirable to use the ready-to-use or ready-to-dilute composition of Fosaprepitant dimeglumine in conjunction with another pharmacologically active agent. For example, the ready-to-use or ready-to-dilute composition of Fosaprepitant dimeglumine may be presented together with another therapeutic agent as a combined preparation for simultaneous, separate, or sequential use for the relief of CINV. A preferred combination comprises the ready-to-use or ready-to-dilute composition of Fosaprepitant dimeglumine and a corticosteroid such as Dexamethasone, Triamcinolone, Flunisolide, Budesonide, etc.; and/or an anti-emetic agent, especially $5HT_3$ receptor antagonists, such as palonosetron, ondansetron, granisetron, tropisetron, decadron, and zatisetron, or $GABA_B$ receptor agonists, such as baclofen. Further, the ready-to-use or ready-to-dilute compositions of Fosaprepitant dimeglumine may be administered in combination with a chemotherapeutic agent such as an alkylating agent, antimetabolite, mitotic inhibitor, or cytotoxic antibiotic, etc.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Stabilized liquid compositions can include excipients according to the following general parameters:

| Ingredients | Quantity (in total composition) |
| --- | --- |
| Fosaprepitant dimeglumine | 50-250 mg |
| Stabilizer | 0-500 mg |
| Solubilizer | 0-5 mL |
| Vehicle | 0-150 mL |
| pH adjusting agent | q.s |

Example 1: Fosaprepitant Ready-To-Use Composition

| Ingredients | Concentration per infusion bags |
| --- | --- |
| Fosaprepitant dimeglumine | 245.3 mg[#] |
| Edetate Disodium | 56.4 mg |
| Albumin solution, 25% | 150 mL |
| Sodium hydroxide (NaOH) 0.1 N/ 0.01 N Hydrochloric acid (HCl) | q.s. to pH 7.2 |

[#]245.3 mg of fosaprepitant dimeglumine is equivalent to 150 mg fosaprepitant free acid Albumin solution (25%) was mixed with edetate disodium, followed by addition of fosaprepitant dimeglumine and pH was adjusted, if required to 7.2. The solution was aseptically filtered (through 0.2 um filter), filled in suitable container and sealed.

Example 2: Fosaprepitant Ready-To-Dilute Composition

| Ingredients | Qty/Vial (5 mL) |
| --- | --- |
| Fosaprepitant dimeglumine | 245.3 mg[#] |
| Edetate Disodium | 56.4 mg |

-continued

| Ingredients | Qty/Vial (5 mL) |
|---|---|
| Albumin solution, 25% | 5 mL |
| Sodium hydroxide (NaOH) 0.1N/ 0.01N Hydrochloric acid (HCl) | q.s. to pH 7.2 |

245.3 mg of fosaprepitant dimeglumine is equivalent to 150 mg fosaprepitant free acid Albumin solution (25%) was mixed with edetate disodium, followed by addition of fosaprepitant dimeglumine and pH was adjusted, if required to 7.2. The solution was aseptically filtered (through 0.2 um filter), filled in suitable container and sealed.

Example 3: Fosaprepitant Ready-To-Dilute Composition

| Ingredient | Qty/Vial (2 mL) |
|---|---|
| Fosaprepitant dimeglumine | 245.3 mg# |
| Glycerin + Ethanol (1:1) | q.s. to 2 mL |

245.3 mg of fosaprepitant dimeglumine is equivalent to 150 mg fosaprepitant free acid Fosaprepitant dimeglumine was dissolved in glycerin and ethanol, and the solution was aseptically filtered (through 0.2 um filter) and packed in suitable container.

Example 4: Fosaprepitant Ready-To-Dilute Composition

| Ingredient | Qty/Vial (5 mL) |
|---|---|
| Fosaprepitant dimeglumine | 245.3 mg# |
| Edetate Disodium | 56.4 mg |
| Albumin solution, 25% | 5.0 mL |
| Sodium caprylate | 482 mg |
| Sodium hydroxide (NaOH) 0.1N/ 0.01N Hydrochloric acid (HCl) | q.s. to pH 7.2 |

245.3 mg of fosaprepitant dimeglumine is equivalent to 150 mg fosaprepitant free acid Albumin solution (25%) was mixed with edetate disodium and sodium caprylate, followed by addition of fosaprepitant dimeglumine and pH was adjusted, if required to 7.2. The solution was aseptically filtered (through 0.2 um filter), filled in suitable container and sealed.

Example 5: Fosaprepitant Ready-To-Dilute Composition

| Ingredient | Qty/Vial (5 mL) |
|---|---|
| Fosaprepitant dimeglumine | 245.3 mg# |
| Albumin | 500 mg |
| Edetate Disodium | 56.4 mg |
| Water | q.s. to 5 mL |

245.3 mg of fosaprepitant dimeglumine is equivalent to 150 mg fosaprepitant free acid Albumin was dissolved in water and mixed with edetate disodium, followed by addition of fosaprepitant dimeglumine and pH was adjusted, if required to 7.2. The solution was aseptically filtered (through 0.2 um filter), filled in suitable container and sealed.

Example 6: Fosaprepitant Ready-To-Dilute Composition

| Ingredients | (I) Qty/Vial (25 mL) | (II) Qty/Vial (50 mL) | (III) Qty/Vial (100 mL) |
|---|---|---|---|
| Fosaprepitant dimeglumine | 245.3 mg# | 245.3 mg# | 245.3 mg# |
| Edetate disodium | 56.4 mg | 56.4 mg | 56.4 mg |
| Albumin solution, 25% | 25 mL | 50 mL | 100 mL |
| Sodium hydroxide (NaOH) 0.1N/0.01N Hydrochloric acid (HCl) | q.s. to pH 7.2 | q.s. to pH 7.2 | q.s. to pH 7.2 |

245.3 mg of fosaprepitant dimeglumine is equivalent to 150 mg fosaprepitant free acid Albumin solution (25%) was mixed with edetate disodium, followed by addition of fosaprepitant dimeglumine and pH was adjusted, if required to 7.2. The solution was aseptically filtered (through 0.2 um filter), filled in suitable container and sealed.

Example 7: Fosaprepitant Ready-To-Dilute Composition

| Ingredient | Qty/Vial (2 mL) |
|---|---|
| Fosaprepitant dimeglumine | 245.3 mg# |
| Dimethylacetamide | q.s. to 2 mL |

245.3 mg of fosaprepitant dimeglumine is equivalent to 150 mg fosaprepitant free acid Fosaprepitant dimeglumine was dissolved in dimethylacetamide, and the solution was aseptically filtered (through 0.2 um filter) and packed in suitable container.

Example 8: Fosaprepitant Ready-To-Dilute Composition

| Ingredient | Qty/Vial (2 mL) |
|---|---|
| Fosaprepitant dimeglumine | 245.3 mg# |
| N-methylpyrrolidone | q.s. to 2 mL |

245.3 mg of fosaprepitant dimeglumine is equivalent to 150 mg fosaprepitant free acid Fosaprepitant dimeglumine was dissolved in N-methylpyrrolidone, and the solution was aseptically filtered (through 0.2 um filter) and packed in suitable container.

Example 9: Fosaprepitant Ready-To-Dilute Composition

| Ingredient | Qty/Vial (2 mL) |
|---|---|
| Fosaprepitant dimeglumine | 245.3 mg# |
| Propylene glycol | 2 gm |

245.3 mg of fosaprepitant dimeglumine is equivalent to 150 mg fosaprepitant free acid Fosaprepitant dimeglumine was dissolved in propylene glycol, and the solution was aseptically filtered (through 0.2 um filter) and packed in suitable container.

Example 10: Fosaprepitant Ready-To-Dilute Composition

| Ingredient | Qty/Vial (2 mL) |
| --- | --- |
| Fosaprepitant dimeglumine | 245.3 mg[#] |
| Glycerin | 0.8 gm |
| Propylene glycol | 0.8 gm |
| Ethanol | q.s. to 2 mL |

[#]245.3 mg of fosaprepitant dimeglumine is equivalent to 150 mg fosaprepitant free acid Fosaprepitant dimeglumine was dissolved in glycerine and propylene glycol, and the solution was aseptically filtered (through 0.2 um filter) and packed in suitable container.

Example 11: Stability Study

The ready-to-use and ready-to-dilute composition Examples 1 to 4 were studied for stability of solution with respect to aprepitant content and physical appearance to evaluate aprepitant precipitation. The results are shown in FIG. 1. All the Examples 1 to 4 were clear in physical appearance indicating no precipitation of aprepitant in the composition. The above mentioned comparison of data confirms the stability of fosaprepitant both ready-to-use and ready-to-dilute compositions of the present invention.

Example 12: Single Dose Comparative Pharmacokinetic Study in Rat

Method and Material:

| Test System | Wistar Rat |
| --- | --- |
| Sex | Male |
| Rationale | Wistar Rats were used as it is commonly used rodent species in the pharmacokinetic evaluation of drugs, and acceptable to the regulatory authorities. |
| Source of animals | Animal Research Facility, Suven Life Sciences Ltd. |
| Total no of animals | 20 |
| Age at study/ Body Weight | 8 to 12 weeks/250 –270 g (±20% variation accepted at the time of dosing) |
| Veterinary Examination | Prior to the final assignment to the study, rats were subjected to veterinary examination to ensure that the selected rats are in a good state of health |
| Animal Identification | Animals were uniquely identified by tail marking with permanent marker. |
| Acclimatization | On receipt from supplier, the animals were examined for external signs of ill health prior to acceptance. After health examination, animals were acclimatized for one week under test conditions. Only animals without any visible signs of illness were used for the study |
| Grouping and Randomization | The animals for the experiment were weighed and arranged in ascending order of their body weights. These stratified body weight of rat were distributed by randomization procedure using Microsoft excel spreadsheet to all the experimental groups, such that body weight variation of animals selected for the study does not exceed ±20% of the mean body weight. |
| Animal catheterization | Under isoflurane anesthesia, all animals were cannulated in right external jugular vein and femoral vein (for intravenous infusion, PE-10 tubing). Rats were surgically implanted with a catheter (external jugular vein, PE-50 tubing) for repeated withdrawal of blood samples (~0.300 mL volume per predetermined blood collection time). For each group, one standby animal was catheterized as backup. Rats were allowed to recover for minimum of 72 h after cannulation before inclusion in study and drug administration. General animal health and cannula patency was confirmed prior to dose administration. |

Test Doses:
EMEND® (Fosaprepitant Dimeglumine) for injection
Test formulation 1—Formulation of Example 1
Vehicle and Dose Formulation:
Preparation of 1 mg/mL EMEND for Injection:
Sterile normal saline (0.9% w/v) was used as a vehicle for dilution and infusion for RLD group.

Step 1: 5 mL 0.9% Sodium Chloride for Injection (normal saline) was aseptically injected into the vial. The vial was swirled gently avoiding shaking and jetting saline into the vial.

Step 2: A bottle filled with 145 mL of normal saline was prepared aseptically.

Step 3: The entire volume from the vial was aseptically withdrawn and transferred into the bottle containing 145 mL of normal saline to yield a total volume of 150 mL and a final concentration of 1 mg/1 mL.

Step 4: The bottle was gently inverted 2-3 times.
Test Formulation:
Fosaprepitant Example 1 (1 mg/mL) was administered without any further dilutions.

Route of administration: Intravenous slow infusion for 20 minutes.

Intravenous Infusion: Infusion system included a swivel (Instech, USA), tubing (PE50 tubing), syringes and an infusion pump (Pico plus—Harvard apparatus). Glass syringes (Hamilton) were fixed on to the infusion pumps; PE50 tubing was used in connecting the glass syringes at one end and to animal at other end. Each rat was administered 8 mg/kg single dose of Fosaprepitant (EMEND®) or Example 1 by IV infusion for 20 min with an Infusion volume of 8 mL/kg.

| Group | Animal ID No. | Dose | Formulation strength (mg/mL) | Infusion volume |
| --- | --- | --- | --- | --- |
| (EMEND ®) | 1-10 | 8 mg/kg | 1 | 8 mL/kg |
| Example 1 | 11-20 | 8 mg/kg | 1 | 8 mL/kg |

Blood Collection and Storage of Samples:

| | |
| --- | --- |
| Site of blood collection | External Jugular vein (via cannulation) |
| Volume of blood collected | 0.30 mL (approx.) at each time point |
| Anticoagulant | Sodium heparin (Stock: 1000 IU/mL; 10 µL/0.30 mL blood) |
| Blood collection time points | 0 (pre-dose), 0.16, 0.33, 0.5, 1, 2, 4, 6, 8, 12, 24 hr post-dose (Total 11 bleedings/rat). |
| Blood centrifugation | 5000 rpm for 5 minutes at 4° C. |
| Plasma storage | −70° C. until analysis (two aliquots of ~0.1 mL each) |

Note:
A pre-dose sample was collected within 1.0 hour prior to dose administration from each rat. Blood samples were kept on ice bath till centrifugation and centrifugation was done within 30 minutes of collection.

On completion of last blood sampling, animals were sacrificed and carcasses discarded.

Bioanalysis: Plasma samples from group were analyzed for aprepitant concentrations. Bioanalysis was performed by fit-for-purpose analytical method using LC-MS/MS.

Figure 2:
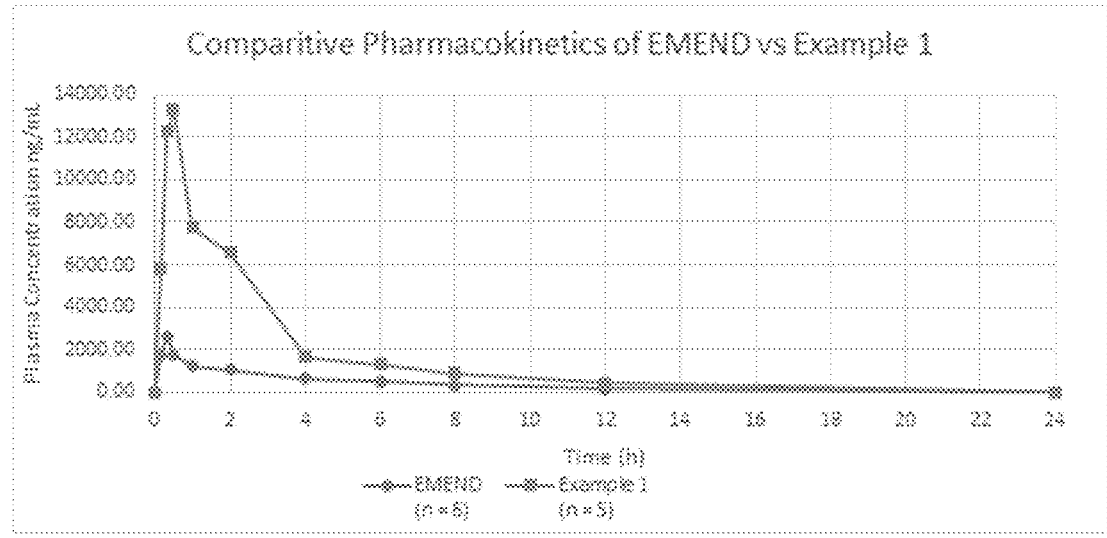
FIG. 2: Comparative pharmacokinetics of fosaprepitant compositions.

Pharmacokinetic Data Analysis and Evaluation:

Phoenix® Software, version 6.4, USA was used for studying Pharmacokinetic parameters such as Cmax, Tmax, Kel, T1/2, AUC (0-t), AUC (0-∞), VD, Geometric means, 90 percent Confidence intervals (CI). Data are presented in FIG. 2.

Example 13: Single Dose Comparative Pharmacokinetic Study in Rat

Method and Material:

| Test System | Wistar Rat |
|---|---|
| Sex | Male |
| Rationale | Wistar Rats were used as it is commonly used rodent species in the pharmacokinetic evaluation of drugs, and acceptable to the regulatory authorities. |
| Source of animals | Animal Research Facility, Suven Life Sciences Ltd. |
| Total no of animals | 30 |
| Age at study/Body Weight | 8 to 12 weeks/220 ± 20 g (±20% variation accepted at the time of dosing) |
| Veterinary Examination | Prior to the final assignment to the study, rats were subjected to veterinary examination to ensure that the selected rats are in a good state of health |
| Animal Identification | Animals were uniquely identified by tail marking with permanent marker. |
| Acclimatization | On receipt from supplier, the animals were examined for external signs of ill health prior to acceptance. After health examination, animals were acclimatized for one week under test conditions. Only animals without any visible signs of illness were used for the study |
| Grouping and Randomization | The animals for the experiment were weighed and arranged in ascending order of their body weights. These stratified body weight of rat were distributed by randomization procedure using Microsoft excel spreadsheet to all the experimental groups, such that body weight variation of animals selected for the study does not exceed ±20% of the mean body weight. |
| Animal catheterization | Under isoflurane anesthesia, all animals were cannulated in right external jugular vein and femoral vein (for intravenous infusion, PE-10 tubing). Rats were surgically implanted with a catheter (external jugular vein, PE-50 tubing) for repeated withdrawal of blood samples (~0.300 mL volume per predetermined blood collection time). For each group, one standby animal was catheterized as backup. Rats were allowed to recover for minimum of 72 h after cannulation before inclusion in study and drug administration. General animal health and cannula patency was confirmed prior to dose administration. |

EMEND® (Fosaprepitant Dimeglumine) for injection

Test formulation 2—Example 2

Test formulation 3—Example 3

Vehicle and Dose Formulation:

Sterile normal saline (0.9% w/v) was used as a vehicle for dilution and infusion.

Emend® Formulation:

Step 1: 5 mL 0.9% Sodium Chloride for Injection (normal saline) was aseptically injected into the vial. The vial was swirled gently avoiding shaking and jetting saline into the vial.

Step 2: A bottle filled with 145 mL of normal saline was prepared aseptically.

Step 3: The entire volume from the vial was aseptically withdrawn and transferred into the bottle containing 145 mL of normal saline to yield a total volume of 150 mL and a final concentration of 1 mg/mL.

Step 4: The bottle was gently inverted 2-3 times.

Test Formulation 2

Step 1: 2 mL formulation was aseptically withdrawn from the vial (75 mg/mL strength).

Step 2: 2 mL formulation was aseptically transferred into 148 mL of normal saline to yield a total volume of 150 mL and a final concentration of 1 mg/mL.

Step 3: The contents were gently mixed before use.

Test Formulation 3

Step 1: 5 mL formulation was aseptically withdrawn from the vial (30 mg/mL strength).

Step 2: 5 mL formulation was aseptically transferred into the container containing 145 mL of normal saline to yield a total volume of 150 mL and a final concentration of 1 mg/mL.

Step 3: The contents were gently mixed before use.

Route of administration: Intravenous slow infusion for 20 minutes.

Intravenous Infusion: Infusion system included a swivel (Instech, USA), tubing (PE50 tubing), syringes and an infusion pump (Pico plus—Harvard apparatus). Glass syringes (Hamilton) were fixed on to the infusion pumps; PE50 tubing was used in connecting the glass syringes at one end and to animal at other end. Each rat was administered 8 mg/kg single dose of Fosaprepitant (EMEND®) or Fosaprepitant (RTD—2 & 3 formulations) by IV infusion for 20 min with an Infusion volume of 8 mL/kg.

| Group | Animal ID No. | Dose | Formulation strength (mg/mL) | Infusion volume |
|---|---|---|---|---|
| EMEND ® | 1-10 | 8 mg/kg | 1 | 8 mL/kg |
| Example 2 | 11-20 | 8 mg/kg | 1 | 8 mL/kg |
| Example 3 | 21-30 | 8 mg/kg | 1 | 8 mL/kg |

Blood Collection and Storage of Samples:

| | |
|---|---|
| Site of blood collection | External Jugular vein (via cannulation) |
| Volume of blood collected | 0.30 mL (approx.) at each time point |
| Anticoagulant | Sodium heparin (Stock: 1000 IU/mL; 10 µL/0.30 mL blood) |
| Blood collection time points | 0 (pre-dose), 0.16, 0.33, 0.5, 1, 2, 4, 6, 8, 12, 24 hr post-dose (Total 11 bleedings/rat). |
| Blood centrifugation | 5000 rpm for 5 minutes at 4° C. |
| Plasma storage | −70° C. until analysis (two aliquots of ~0.1 mL each) |

Note:
A pre-dose sample was collected within 1.0 hour prior to dose administration from each rat. Blood samples were kept on ice bath till centrifugation and centrifugation was done within 30 minutes of collection.

On completion of last blood sampling, animals were sacrificed and carcasses discarded.

Bioanalysis: Plasma samples from group were analyzed for aprepitant concentrations. Bioanalysis was performed by fit-for-purpose analytical method using LC-MS/MS.

Figure 3:
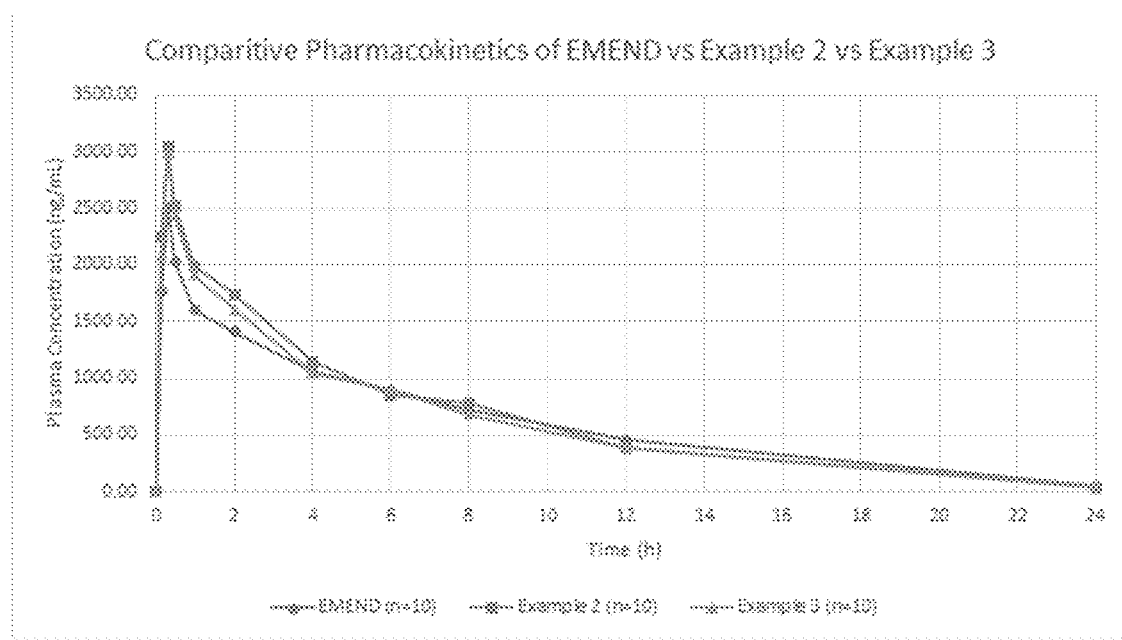
FIG. 3: Comparative Pharmacokinetics of fosaprepitant compositions.

Pharmacokinetic Data Analysis and Evaluation:

Phoenix® Software, version 6.4, USA was used for studying Pharmacokinetic parameters such as Cmax, Tmax, Kel, T1/2, AUC (0-t), AUC (0-∞), VD, Geometric means, 90 percent Confidence intervals (CI). Data are presented in FIG. 3.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A liquid composition comprising:
fosaprepitant or a salt thereof, an aqueous albumin vehicle, and at least one stabilizer selected from fatty acid metal salts, antioxidants, and chelating agents,
wherein after storage at 2-8° C. for at least 1 month, aprepitant is present in an amount concentration of no more than 10%.

2. The liquid composition according to claim 1, comprising a chelating agent selected from the group consisting of ethylenediaminetetraacetic acid, hydroxyethylethylenediaminetriacetic acid, diethylenetriaminepentaacetic acid, nitrilotriacetic acid, ethanol diglycine, 1,3-propylenediaminetetraacetic acid, or a pharmaceutically acceptable salt thereof.

3. The liquid composition according to claim 2, wherein the chelating agent comprises ethylenediaminetetraacetic acid or pharmaceutically acceptable salt thereof.

4. The liquid composition according to claim 1, wherein the aqueous albumin vehicle comprises a 25% aqueous albumin vehicle.

5. The liquid composition according to claim 1, wherein the fosaprepitant is fosaprepitant dimeglumine.

6. The liquid composition according to claim 1, further comprising an additional agent for the treatment of chemotherapy-induced nausea and vomiting (CINV).

7. The liquid composition according to claim 6, wherein the additional agent comprises a corticosteroid, a $5HT_3$ receptor antagonist, $GABA_B$ receptor agonist, or a combination thereof.

8. The liquid composition according to claim 7, wherein the additional agent comprises dexamethasone, triamcinolone, flunisolide, budesonide, palonosetron, ondansetron, granisetron, tropisetron, decadron, zatisetron, or baclofen.

9. A method of treating chemotherapy-induced nausea and vomiting (CINV), wherein the method comprises administering a liquid pharmaceutical composition according to claim 1.

10. The method according to claim 9, comprising administering at least one additional agent for the treatment of chemotherapy-induced nausea and vomiting (CINV).

11. The method according to claim 10, wherein the additional agent comprises dexamethasone, triamcinolone, flunisolide, budesonide, palonosetron, ondansetron, granisetron, tropisetron, decadron, zatisetron, baclofen, or a combination thereof.

12. A liquid composition comprising fosaprepitant or a salt thereof, a solubilizer comprising at least one alcohol, at least one glycol, or a combination thereof, wherein after storage at 2-8° C. for at least 1 month, aprepitant is present in an amount concentration of no more than 10%, wherein the composition is ready-to-use or ready-to-dilute.

13. The liquid composition according to claim 12, wherein the alcohol comprises ethanol, octanol, glycofurol or a mixture thereof.

14. The liquid composition according to claim 12, comprising a glycol comprising propylene glycol, glycerol, polyethylene glycol, or a mixture thereof.

15. The liquid composition according to claim 12, comprising ethanol and propylene glycol.

16. The liquid composition according to claim 12, further comprising an additional agent for the treatment of chemotherapy-induced nausea and vomiting (CINV).

17. The liquid composition according to claim 12, wherein the additional agent comprises a corticosteroid, a $5HT_3$ receptor antagonist, $GABA_B$ receptor agonist, or a combination thereof.

18. The liquid composition according to claim 12, wherein the additional agent comprises dexamethasone, triamcinolone, flunisolide, budesonide, palonosetron, ondansetron, granisetron, tropisetron, decadron, zatisetron, or baclofen.

19. A method of treating chemotherapy-induced nausea and vomiting (CINV), wherein the method comprises administering a liquid pharmaceutical composition according to claim 12.

20. The method according to claim 19, comprising administering at least one additional agent for the treatment of chemotherapy-induced nausea and vomiting (CINV).

21. The method according to claim 20, wherein the additional agent comprises dexamethasone, triamcinolone, flunisolide, budesonide, palonosetron, ondansetron, granisetron, tropisetron, decadron, zatisetron, baclofen, or a combination thereof.

* * * * *